(12) United States Patent
Dayanim

(10) Patent No.: US 8,926,949 B2
(45) Date of Patent: Jan. 6, 2015

(54) COMPOSITION FOR ORAL HEALTH TREATMENT AND RELATED METHODS OF USE

(76) Inventor: Rebecca Dayanim, Santa Monica, CA (US)

( * ) Notice: Subject to any disclaimer, the term of this patent is extended or adjusted under 35 U.S.C. 154(b) by 241 days.

(21) Appl. No.: 13/097,297

(22) Filed: Apr. 29, 2011

(65) Prior Publication Data

US 2012/0052022 A1   Mar. 1, 2012

Related U.S. Application Data

(60) Provisional application No. 61/354,879, filed on Jun. 15, 2010.

(51) Int. Cl.
*A61Q 11/00* (2006.01)
*A61K 8/24* (2006.01)
*A61K 8/97* (2006.01)
*A61K 8/66* (2006.01)
*A61K 31/355* (2006.01)
*A61K 31/375* (2006.01)
*A61K 36/185* (2006.01)
*A61K 38/44* (2006.01)
*A61K 45/06* (2006.01)

(52) U.S. Cl.
CPC ............... *A61K 8/24* (2013.01); *A61K 31/355* (2013.01); *A61K 31/375* (2013.01); *A61K 36/185* (2013.01); *A61K 38/44* (2013.01); *A61K 45/06* (2013.01); *A61K 8/66* (2013.01); *A61Q 11/00* (2013.01); *A61K 8/97* (2013.01); *Y10S 514/901* (2013.01)
USPC .................. 424/49; 424/50; 424/58; 424/57; 514/901

(58) Field of Classification Search
USPC .................. 424/49, 50, 57, 58, 401; 514/901
See application file for complete search history.

(56) References Cited

U.S. PATENT DOCUMENTS

| 4,269,822 | A * | 5/1981 | Pellico et al. ................... 424/50 |
| 5,262,151 | A * | 11/1993 | Montgomery .................. 424/50 |
| 6,228,347 | B1 * | 5/2001 | Hersh .............................. 424/49 |
| 2007/0081952 | A1 * | 4/2007 | Cardon ........................... 424/50 |
| 2007/0275104 | A1 * | 11/2007 | Kornman et al. ............. 424/729 |
| 2008/0008665 | A1 * | 1/2008 | Ramji et al. .................... 424/48 |
| 2010/0183524 | A1 | 7/2010 | Zielinski et al. |

OTHER PUBLICATIONS

Medline Plus, Antioxidants, pp. 1-2 Oct. 2007.*

* cited by examiner

*Primary Examiner* — Lezah Roberts
(74) *Attorney, Agent, or Firm* — Quarles & Brady, LLP

(57) ABSTRACT

The present invention provides compositions and related methods for oral health treatment of a subject. Compositions of the invention include an anti-oxidant enzyme, an anti-inflammatory agent, and a pharmaceutically acceptable buffer. In certain embodiments, the compositions are administered to the subjection in conjunction with teeth whitening, oral surgery, oral pathology treatment, endodontic therapy, periodontal therapy, dental restoration, preventative tooth cleaning, or subsequent to a pro-oxidant.

4 Claims, No Drawings

COMPOSITION FOR ORAL HEALTH TREATMENT AND RELATED METHODS OF USE

CROSS-REFERENCE TO RELATED APPLICATIONS

This application claims the benefit of U.S. Provisional Application No. 61/354,879, filed Jun. 15, 2010, the entirety of which is hereby incorporated by reference for all purposes.

FIELD OF THE INVENTION

This invention relates to compositions for oral health treatment. More particularly, the present invention is directed to compositions and methods useful in treating free radical species in the oral cavity of a human subject.

BACKGROUND OF THE INVENTION

In a living organism, free radicals produced by oxidation reactions can propagate chain reactions that damage cells making up the organism's tissues and organs. Anti-oxidants present in the living organism terminate these chain reactions by removing free radical intermediates, and inhibit other oxidation reactions by being oxidized themselves. Anti-oxidants are often reducing chemical agents such as thiols, ascorbic acid or polyphenols. Vitamins C and E represent specific examples of such reducing chemical agents.

In addition, living organisms have evolved complex anti-oxidant enzyme-based systems to reduce dangerous oxidative stress and cell damage caused by free radicals. A wide array of enzymes are present in living organisms to combat free radical damage including, but not limited to, catalases, superoxide dismutases and peroxidases.

However, it is understood that certain treatments performed on the living body result in dangerously high local concentrations of free radicals. Such treatments bring the body in to contact with free radical concentrations far exceeding those formed by oxidative reactions normal to healthy physiological processes. For example, the oxidative chemicals utilized in a general teeth whitening procedure generate an undesirably high concentration of free radicals in the mouth of a dental patient during the whitening procedure. Accordingly, it is beneficial to immediately reduce the free radical concentration following such a procedure to a concentration level which lessens the damage to living cells comprising the patient's oral cavity, including the teeth, gums, supporting bone, and soft tissues of the mouth such as the tongue and lips. In view of the current state of the art, there exists a pressing need and considerable market potential for compositions useful in reducing the hazard of free radicals associated with treatment of the living body.

SUMMARY OF THE INVENTION

In a first aspect, the present invention provides a composition comprising: (a) an anti-oxidant enzyme; (b) an anti-inflammatory agent; and (c) a pharmaceutically acceptable buffer.

The anti-oxidant enzyme is preferably a catalase, superoxide dismutase, methionine reductase, glutathione peroxidase, superoxide reductase, peroxidase, or a mixture thereof.

The anti-inflammatory agent is preferably a fruit or vegetable extract, but may alternatively be an agent such as chlorohexidine, chlorohexidine gluconate, doxycycline, tetracycline, minocycline, or a mixture thereof.

Particularly preferred anti-inflammatory agents are extract of pomegranate, cranberry, acai berry, rooibos, green tea, avocado, or a mixture thereof.

The pharmaceutically acceptable buffer included in the composition is preferably $K_2HPO_4$, $KH_2PO_4$, $Na_2HPO_4$, $NaH_2PO_4$, $H_2CO_3$, $NaHCO_3$, $Na_2CO_3$, $K_2CO_3$, $CaCO_3$, or a mixture thereof.

In various alternative embodiments, the composition of the invention may further contain one or more of a flavor additive, vitamin E, vitamin C, an anti-cavity agent, or an anti-sensitivity agent.

Compositions of the invention may be provided in the form of, e.g., a dental rinse, powder, gel, varnish, toothpaste, lozenge, gum, floss, tablet or injectable dosage.

In a particularly preferred embodiment, the anti-oxidant enzyme is catalase, the anti-inflammatory agent is pomegranate, and the pharmaceutically acceptable buffer includes $K_2HPO_4$ and $KH_2PO_4$.

In preferred formulations, the composition is provided in the form of a dental rinse having a pH of about 4.0 to about 11.0, more preferably about 7.0.

In another aspect the invention encompasses methods for providing an oral health treatment to a subject. Such methods includes steps of administering to a subject's oral cavity an inventive composition described herein, whereby an oral health treatment is provided to the subject.

The oral health treatment may be provided to the subject in conjunction with teeth whitening, oral surgery, oral pathology treatment, endodontic therapy, periodontal therapy, dental restoration, general preventative tooth cleaning, or subsequent to a pro-oxidant. In particular, the oral health treatment is provided to the subject in conjunction with internal or external dental bleaching, tooth extraction, hard or soft tissue surgery, root canal therapy, apical surgery, debridement, scaling, root planing, composite or bonding procedure, or a prophylactic procedure.

A preferred mode of administration to a subject is by dental rinse.

In yet another aspect, the invention provides a method of treating free radicals in a subject. Such a method includes steps of administering an anti-oxidant enzyme to a subject whereby free radicals are treated in the subject.

The method may be provided for a wide range of applications including, e.g., oral care, facial care, skin care, nasal care, ear care, hair care, or chest, back, waist, abdomen or extremity care.

Of course, the present invention contemplates the use of a composition described herein for the manufacture of a dental rinse, powder, gel, varnish, toothpaste, lozenge, gum, floss, tablet or injectable dosage for oral health treatment of a subject as well as the present compositions' use in oral health treatment of a subject.

Other objects, features and advantages of the present invention will become apparent after review of the below detailed description, examples and claims.

DETAILED DESCRIPTION OF THE INVENTION

It is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The term "administration" and variants thereof (e.g., "administering" a composition) in reference to an inventive composition mean providing the composition to an individual in need of treatment.

As used herein, the term "composition" is intended to encompass a chemical composition comprising the specified ingredients, as well as any product which results, directly or indirectly, from combining the specified ingredients.

By "pharmaceutically acceptable" is meant that the ingredients of the composition must be pharmaceutically compatible with each other and not deleterious to the recipient thereof.

The term "subject" as used herein refers to an animal, preferably a mammal, most preferably a human, who has been the object of treatment, observation or experiment. Furthermore, the terms "human," "patient" and "subject" are used interchangeably herein.

The term "effective amount" as used herein means that amount of composition that elicits the biological or medicinal response in a tissue, system, animal or human that is being sought by a researcher, dentist, veterinarian, medical doctor or other clinician. In one embodiment, the effective amount is a "therapeutically effective amount" for the alleviation of the symptoms of the disorder or condition being treated. In another embodiment, the effective amount is a "prophylactically effective amount" for prophylaxis of the symptoms of the disorder or condition being prevented. The term also includes the amount of anti-oxidant enzyme sufficient to reduce one or more free radical species or related intermediates in a statistically significant manner (i.e., an "free radical reducing amount").

"Treating" or "treatment" of any condition or disorder refers, in one embodiment, to ameliorating the condition or disorder (i.e., arresting or reducing the development of the condition or at least one of the clinical symptoms thereof). In another embodiment "treating" or "treatment" refers to ameliorating at least one physical parameter, which may not be discernible by the subject. In yet another embodiment, "treating" or "treatment" refers to modulating the condition or disorder, either physically, (e.g., stabilization of a discernible symptom), physiologically, (e.g., stabilization of a physical parameter), or both. In yet another embodiment, "treating" or "treatment" refers to delaying the onset of the condition or disorder, or even preventing the same.

As used herein, "vitamin E" is a generic term for tocopherols and tocotrienols. Vitamin E is a family of $\alpha$-, $\beta$-, $\gamma$-, and $\delta$-tocopherols and corresponding four tocotrienols. Of these, $\alpha$-tocopherol (also written as alpha-tocopherol) has been most studied as it has the highest bioavailability.

"Vitamin C" is a water-soluble vitamin important for healthy skin, teeth, bones, and blood vessels. The term includes both acid (i.e., ascorbic acid) and salts (e.g., sodium ascorbate) of the vitamin.

"Oral health" refers to the health of the oral cavity, including the mouth, teeth, gums, supporting bone, and soft tissues of the mouth such as the tongue and lips.

The present invention is based on the inventor's success in identifying certain compositions useful in treating free radicals in the living body. Accordingly, a first aspect of the invention is directed to compositions useful in the treatment of free radicals in the oral cavity of a subject in connection with various dental procedures. Such compositions include: (a) an anti-oxidant enzyme; (b) an anti-inflammatory agent; and (c) a pharmaceutically acceptable buffer.

The anti-oxidant enzyme is generally capable of reducing one or more free radical species and is an enzyme such as, for example, a catalase, superoxide dismutase, methionine reductase, glutathione peroxidase, superoxide reductase, peroxidase, or a mixture thereof. Catalase is a particularly preferred anti-oxidant enzyme in the compositions described and claimed herein. Anti-oxidant enzymes are readily available to the public. For example, catalase suitable for use in the present invention is available from Sigma-Aldrich, Genencor, or Biocatalysts (as described in Examples 1 and 2).

The anti-inflammatory agent is preferably a fruit or vegetable extract such as an extract of pomegranate, cranberry, acai berry, rooibos, green tea, avocado, or a mixture thereof. Fruit and vegetable extracts appropriate for the present formulations are available from, for example, PureBulk Nutrition of Myrtle Point, Oreg. Pomegranate extract is a particularly preferred anti-inflammatory agent, also available from PureBulk Nutrition. Anti-inflammatory agents suitable for use in the invention shall not be limited to fruit or vegetable extracts but may further include various synthetic or chemical-based agents such as, e.g., chlorohexidine, chlorohexidine gluconate, doxycycline, tetracycline, or minocycline.

Compositions of the invention include a pharmaceutically acceptable buffer selected from, for example, $K_2HPO_4$, $KH_2PO_4$, $Na_2HPO_4$, $NaH_2PO_4$, $H_2CO_3$, $NaHCO_3$, $Na_2CO_3$, $K_2CO_3$, $CaCO_3$ or mixtures thereof. In particular, buffer systems made up of monobasic potassium phosphate and dibasic potassium phosphate, available from Sigma-Aldrich, represent a preferred combination of acceptable buffer for use in the invention. Buffer systems useful in the invention are, in general, provided in an aqueous solution consisting of a mixture of a weak acid and its conjugate base or a weak base and its conjugate acid. The buffer system has the property that the pH of the solution changes very little when a small amount of strong acid or base is added to it.

In alternative embodiments, inventive compositions may include one or more additional components selected from a flavor additive, vitamin E, vitamin C, an anti-cavity agent, and an anti-sensitivity agent.

Suitable flavor additives include sugar alcohols such as xylitol, mannitol, sorbitol, erythritol, maltitol, lactitol, or mixtures thereof. Herbal sweeteners such as stevia or artificial sweeteners such as aspartame or sucralose may be employed in addition to or as alternatives to sugar alcohols. Xylitol, available from PureBulk Nutrition of Myrtle Point, Oreg., if a preferred flavor additive in the present compositions. Compositions according to the invention may be prepared in a variety of flavors including, but not limited to, mint, cinnamon, citrus, berry or pomegranate.

Vitamins C and/or E are optionally provided in compositions of the invention and are readily available in pharmaceutically acceptable forms from Sigma-Aldrich.

As well, compositions according to the invention may optionally include anti-cavity agent and/or an anti-sensitivity agent. Suitable anti-cavity agents include, for example, sodium fluoride available from Sigma-Aldrich. Appropriate anti-sensitivity agents include, e.g., calcium phosphate, calcium acetate, or calcium chloride, also available from Sigma-Aldrich.

The invention encompasses various formulation forms of the composition, including, but not limited to, a dental rinse, powder, gel, varnish, toothpaste, lozenge, gum, floss, tablet or injectable dosage. A preferred formulation of dental rinse is described below in the Examples section. The exemplary dental rinse includes the anti-oxidant enzyme catalase, the anti-inflammatory agent pomegranate extract in which the active ingredient is ellagic acid, the pharmaceutically acceptable buffer system of $K_2HPO_4$ and $KH_2PO_4$, and the flavor additive xylitol. Such dental rinses according to the invention may range in pH between about 4 to about 11, more preferably about 6 to about 8, and most preferably about 7.

In another aspect, the invention encompasses a method for providing an oral health treatment to a subject. Such a method includes steps of administering to a subject's oral cavity a composition described and claimed herein, whereby an oral health treatment is provided to the subject.

The method is provided to the subject in conjunction with a wide variety of dental procedures including, for example, teeth whitening, oral surgery, oral pathology treatment, endodontic therapy, periodontal therapy, dental restoration, general preventative tooth cleaning, or subsequent to a pro-oxidant's use. More particularly, the method may be provided in conjunction with internal or external dental bleaching, tooth extraction, hard or soft tissue surgery, root canal therapy, apical surgery, debridement, scaling, root planing, composite or bonding procedure, or a prophylactic procedure. In other embodiments, the method is provided as an oral health treatment in conjunction with a subject's regular regimen of oral health care, such as a daily mouth wash.

In yet another aspect, the invention provides a method of treating free radicals in a subject including the step of administering an anti-oxidant enzyme to a subject, whereby free radicals are treated in the subject. Such a method is envisioned for use in a plethora of health-related areas such as, for example, oral care, facial care, skin care, nasal care, ear care, hair care, or chest, back, waist, abdomen or extremity care.

The invention further contemplates the use of a composition as described and claimed herein for the manufacture of a dental rinse, powder, gel, varnish, toothpaste, lozenge, gum, floss, tablet or injectable dosage for oral health treatment of a subject as well as the various compositions' use in treatment of a subject. Methods of formulating/manufacturing inventive compositions (alternatively termed "medicaments") for the treatment of free radicals in a subject, including treatment of free radicals of in the oral cavity of a subject are, of course, within the invention's scope.

The following Examples are offered by way of illustration and not by way of limitation, Indeed, various modifications of the invention in addition to those shown and described herein will become apparent to those skilled in the art from the foregoing description and the following examples and fall within the scope of the appended claims.

EXAMPLES

Example 1

A dental rinse formulation for administration to a human subject after a teeth whitening procedure was prepared by dissolving the following ingredients in distilled water to a final volume of 0.24 liters and adjusting the pH to 7.0.

catalase (see options below)
    10 mg pomegranate extract/ellagic acid (PureBulk Nutrition, Myrtle Point, Oreg.)
    0.365 grams monobasic potassium phosphate (Sigma-Aldrich)
    1.62 grams dibasic potassium phosphate (Sigma-Aldrich)
    10 grams xylitol (PureBulk Nutrition, Myrtle Point, Oreg.)
    3.6 ml natural mint blend flavor (GSB, Kennesaw, Ga.)

Suitable catalases and amounts for inclusion in the above formulation are:
    a) 616 uL catalase from *Aspergillus niger* (6800-8000 Baker units/g; Genencor, Rochester, N.Y.); or
    b) 7.62 uL catalase from *Micrococcus lysodeikticus* (550 Baker units/g; Biocatalysts, Wales, UK).

Example 2

An alternative dental rinse formulation for administration to a human subject after a teeth whitening procedure was prepared by dissolving the following ingredients in distilled water to a final volume of 0.24 liters and adjusting the pH to 7.0.

0.74 μL catalase from *Micrococcus lysokeikticus* (170,000 units/mL; Sigma-Aldrich)
    10 mg pomegranate extract/ellagic acid (PureBulk Nutrition, Myrtle Point, Oreg.)
    0.686 grams monobasic potassium phosphate (Sigma-Aldrich)
    1.212 grams dibasic potassium phosphate (Sigma-Aldrich)
    5 grams xylitol (PureBulk Nutrition, Myrtle Point, Oreg.)

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. All publications, patents and patent applications cited herein are hereby incorporated by reference in their entirety for all purposes.

What is claimed is:

1. A method for reducing an elevated free radical concentration that results from a dental procedure performed in the oral cavity of a human subject, comprising administering to a subject's oral cavity a dental rinse comprising (a) a free radical reducing amount of anti-oxidant enzyme selected from the group consisting of catalase, superoxide dismutase, methionine reductase, glutathione peroxidase, superoxide reductase, peroxidase, and mixtures thereof; (b) an effective amount of anti-inflammatory agent selected from the group consisting of an extract of pomegranate, cranberry, acai berry, rooibos, green tea, avocado, and mixtures thereof; and (c) a pharmaceutically acceptable buffer comprising $K_2HPO_4$, and $KH_2PO_4$, whereby an elevated free radical concentration that results from the dental procedure performed in the oral cavity of the human subject is reduced.

2. The method of claim 1, wherein said method is provided to the subject in conjunction with teeth whitening, oral surgery, oral pathology treatment, endodontic therapy, periodontal therapy, dental restoration, general preventative tooth cleaning, or subsequent to a pro-oxidant.

3. The method of claim 1, wherein said method is provided to the subject in conjunction with internal or external dental bleaching, tooth extraction, hard or soft tissue surgery, root canal therapy, apical surgery, debridement, scaling, root planing, composite or bonding procedure, or a prophylactic procedure.

4. The method of claim 1, wherein the anti-oxidant enzyme is catalase; and the anti-inflammatory agent is pomegranate.

\* \* \* \* \*